(12) United States Patent
Kim

(10) Patent No.: US 11,872,065 B2
(45) Date of Patent: Jan. 16, 2024

(54) X-RAY IMAGING STAND WITH STRAIGHT ARM STRUCTURE

(71) Applicant: Shin Young For M co., Ltd, Namyangju-si (KR)

(72) Inventor: Ik-Han Kim, Seoul (KR)

(73) Assignee: Shin Young For M co., Ltd, Namyangju-si (KR)

( * ) Notice: Subject to any disclaimer, the term of this patent is extended or adjusted under 35 U.S.C. 154(b) by 185 days.

(21) Appl. No.: 17/493,772

(22) Filed: Oct. 4, 2021

(65) Prior Publication Data

US 2022/0117569 A1 Apr. 21, 2022

(30) Foreign Application Priority Data

Oct. 15, 2020 (KR) .......................... 10-2020-0133212

(51) Int. Cl.
*A61B 6/00* (2006.01)
(52) U.S. Cl.
CPC ............ *A61B 6/4435* (2013.01); *A61B 6/505* (2013.01); *A61B 2562/0257* (2013.01)
(58) Field of Classification Search
None
See application file for complete search history.

(56) References Cited

U.S. PATENT DOCUMENTS

| 7,748,900 B2 * | 7/2010 | Maschke ............... A61B 6/4458 378/197 |
| 2018/0070901 A1 * | 3/2018 | Gabella ................. A61B 6/102 |

FOREIGN PATENT DOCUMENTS

| JP | 06-169904 A | 6/1994 |
| JP | 2016-523108 A | 8/2016 |
| KR | 10-2013-0005905 A | 1/2013 |
| KR | 20-0490677 Y1 | 12/2019 |

OTHER PUBLICATIONS

Office Action of Korean Patent Application No. 10-2020-0133212 dated Apr. 12, 2022.

* cited by examiner

*Primary Examiner* — Hoon K Song
(74) *Attorney, Agent, or Firm* — Revolution IP, PLLC

(57) ABSTRACT

Proposed is an X-ray imaging stand with a straight arm structure, the X-ray imaging stand including a detector comprising an X-ray detection module and a detector arm configured to support the X-ray detection module, an imaging module comprising an X-ray imaging tube and a tube arm configured to support the X-ray imaging tube, a main arm, each of the detector and the imaging module being connected to the main arm, and a stand main-body configured to force the main arm to ascend and descend and to be rotated, wherein the detector and the imaging module are configured in such a manner as to have the same weight, and the detector arm and the tube arm are both accommodated within the main arm, and are moved slidably in conjunction with each other in such a manner as to expand and contract in opposite directions with the main arm in between.

6 Claims, 5 Drawing Sheets

# X-RAY IMAGING STAND WITH STRAIGHT ARM STRUCTURE

CROSS REFERENCE TO RELATED APPLICATION

The present application claims priority to Korean Patent Application No. 10-2020-0133212, filed Oct. 15, 2020, the entire contents of which is incorporated herein for all purposes by this reference.

BACKGROUND OF THE INVENTION

Field of the Invention

The present disclosure relates to an X-ray imaging stand and, more particularly, to an X-ray imaging stand with a straight arm structure, the X-ray imaging stand being configured in such a manner as to be expandable and contractable in opposite directions with a main arm in between and thus being installed in a small space and being driven with small motive power.

Description of the Related Art

Generally, a medical X-ray diagnosis apparatus is used for performing radiographic inspection of the human body and thus obtaining an image thereof. Through X-rays, this medical X-ray diagnosis apparatus analyzes whether or not the bones in the chest, head, spine, or injured body portion is damaged.

Normally, the medical X-ray diagnosis apparatus used in a hospital means an apparatus detecting X-rays that are emitted from an X-ray tube and pass through an object subject to imaging, such as an animal or a patient's body. The medical X-ray diagnosis apparatus here includes an X-ray detection device detecting X-rays that are emitted from the X-ray tube and pass through the object subject to imaging. This X-ray detection device is normally also referred to as an "X-ray detector (DR)".

The X-ray tube and the X-ray detector may be configured to be mounted on a ceiling-type X-ray imaging apparatus that includes a post-frame, on which a detector and the like are mounted, and a main body driving the post-frame. The post-frame and the main body are mounted on a guide rail installed on a ceiling of an inspection room. However, in the case of the ceiling-type X-ray imaging apparatus, the guide rail and the like are not easy to mount on the ceiling of the inspection room. Thus, there is a problem in that the ceiling-type X-ray imaging apparatus is limited in installation to a specific place and is inconvenient to move or transport.

To this end, a stand-type X-ray imaging apparatus capable of being installed in the upright position on a floor has been proposed. The detector and the like of the stand-type X-ray imaging apparatus are mounted on an imaging stand. The detector and the like are configured to capture an image of a patient's body portion subject to inspection while ascending and descending along a length direction of the imaging stand by driving a drive motor or through a manual operation.

A stand for an X-ray imaging apparatus in the related art is equipped with a weight balance in order to balance by a counterweight a weight of an X-ray imaging tube or X-ray detection module mounted on the stand in such a manner as to smoothly ascend and descent through the manual operation. However, an increase in the size of the X-ray imaging tube or the X-ray detection module increases the size of the weight balance. Accordingly, a length of the weight balance is also increased. Thus, a height of the stand itself needs to be increased to provide a sufficient space in which the X-ray imaging tube or the X-ray detection module ascends or descends, as well as a space occupied by the weight balance.

However, a building is limited to a predetermined ceiling height. For this reason, there occurs a problem in that the X-ray imaging stand that exceeds a predetermined size cannot be installed within the building.

In addition, whenever necessary, a distance between the X-ray imaging tube and the X-ray detection module needs to be increased by moving the X-ray imaging tube or the X-ray detection tube. For this reason, there is a need to greatly increase a length of a C-type arm or a straight arm. Thus, there occurs a problem in that an overall size of the X-ray imaging stand needs to be increased.

The foregoing is intended merely to aid in the understanding of the background of the present disclosure, and is not intended to mean that the present disclosure falls within the purview of the related art that is already known to those skilled in the art.

SUMMARY OF THE INVENTION

An objective of the present disclosure is to provide an X-ray imaging stand capable of being installed in a small space and of including an arm that is expandable and contractable over a long distance.

Another object of the present disclosure is to provide an X-ray imaging stand capable of moving an X-ray detection module or an X-ray imaging tube with small motive power.

The X-ray imaging stand with a straight arm structure according to the present disclosure, is configured in such a manner that the X-ray detection module and the X-ray tube arm are moved away from or toward each other in conjunction with each other with a main arm in between. Accordingly, the X-ray imaging stand is expandable and contractable in opposite directions and thus is installable in a small space.

In addition, a detector and an imaging tube are configured to have the same weight. Accordingly, the main arm may maintain weight equilibrium because the weights on both sides thereof are the same. Therefore, with small motive power, it is possible that the detector and the imaging module are driven slidably for expansion and contraction.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 7A is a view illustrating a state where the detector arm and the tube arm according to the present disclosure are close to each other with the main arm in between, and FIG. 7B is a view illustrating a state where the detector arm and the tube arm are moved away from each other with the main arm in between.

DETAILED DESCRIPTION OF THE INVENTION

Figure 1:
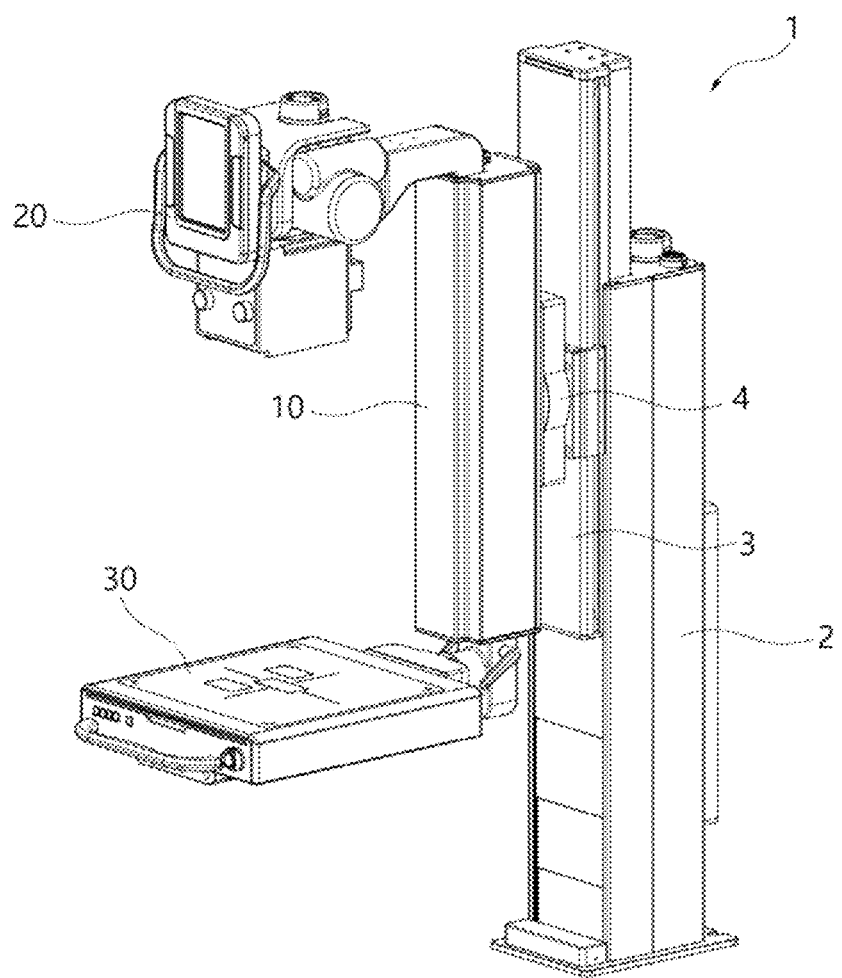
FIG. 1 is a perspective view illustrating an X-ray imaging stand according to the present disclosure.
Figure 2:
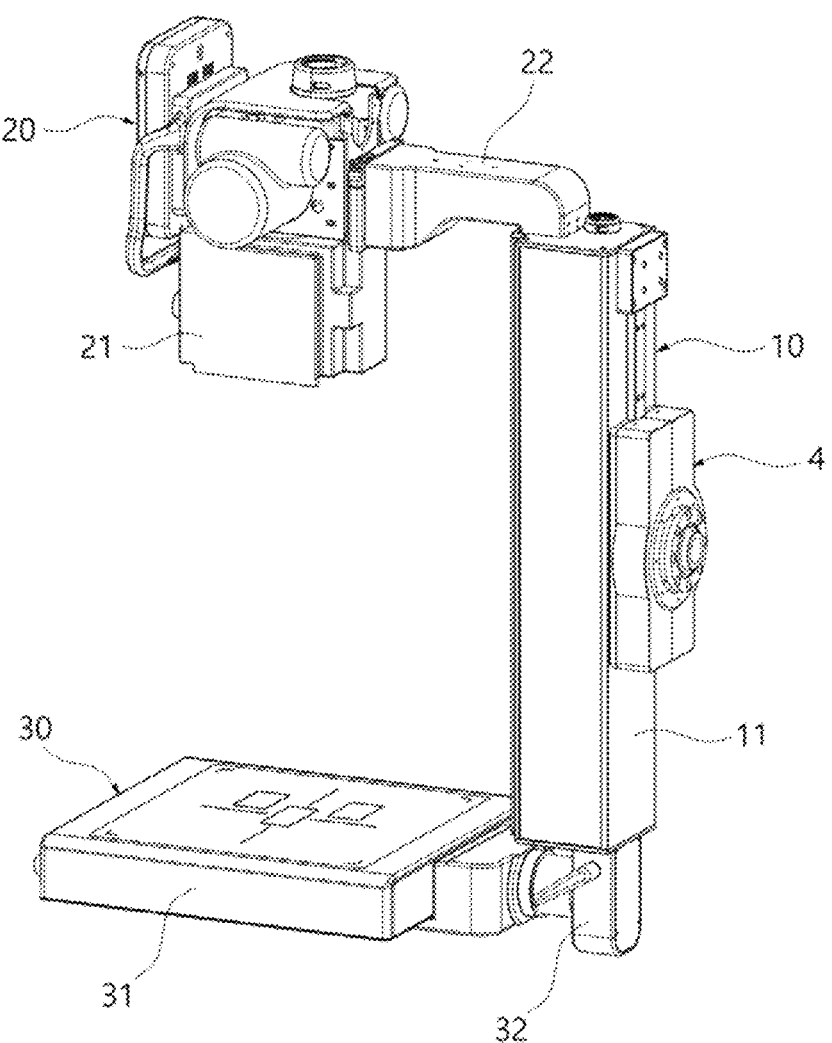
FIG. 2 is a view illustrating a detector, an imaging module, and a main arm according to the present disclosure.

An X-ray imaging stand with a straight-arm structure according to an embodiment of the present disclosure will be described in detail below with reference to the accompanying drawings.

As illustrated in FIGS. 1 to 7, an X-ray imaging stand 1 according to the present disclosure includes an imaging module 20, a detector 30, and a stand main-body 2.

The stand main-body 2 is supported in the upright position on a floor. A slide guide portion 3 is mounted on a front surface of the stand main-body 2. The slide guide portion 3 is mounted in a manner that is movable slidably upward and downward along a guiding line provided on the stand main-body 2. An arm connection portion 4 is formed on the slide guide portion 3.

The arm connection portion 4 is mounted in a manner that is ascendable and descendible along a guide rail provided on the slide guide portion 3 in a state of being fastened to the slide guide portion 3. In addition, the arm connection portion 4 is mounted in a manner that is rotatable about the slide guide portion 3.

A main arm 10 is mounted on the arm connection portion 4. With ascending, descending, and rotation of the arm connection portion 4, the main arm 10 ascends, descends, and rotates in a corresponding manner. The main arm 10 has the shape of approximately a rectangular parallelepiped with long faces and is protected by a casing 11 formed by a plurality of panels.

Figure 3:
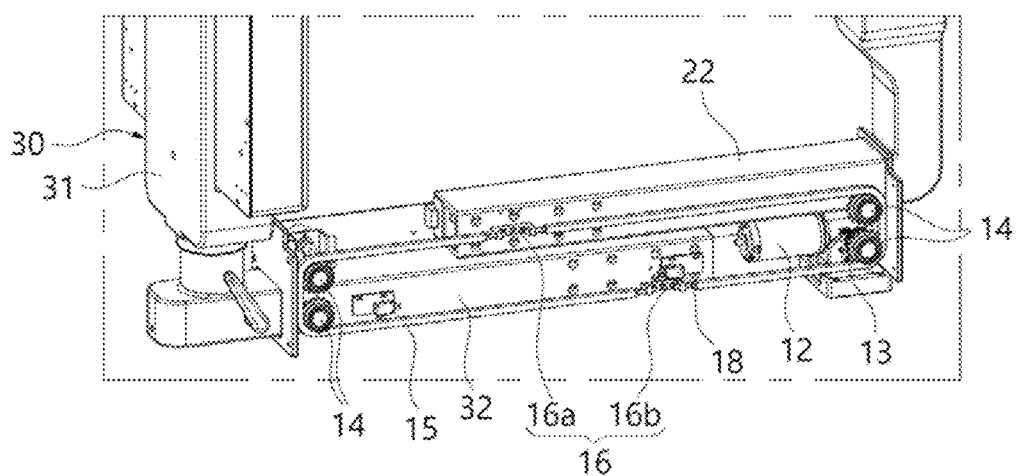
FIG. 3 is a perspective view illustrating a cut-away portion of the main arm.
Figure 4:
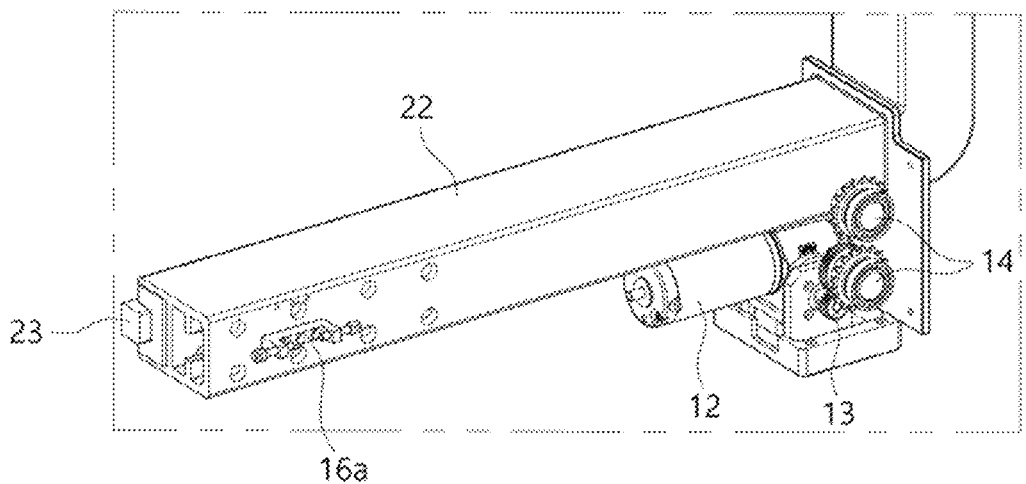
FIG. 4 is a view illustrating a tube arm of an imaging module according to the present disclosure.
Figure 5:
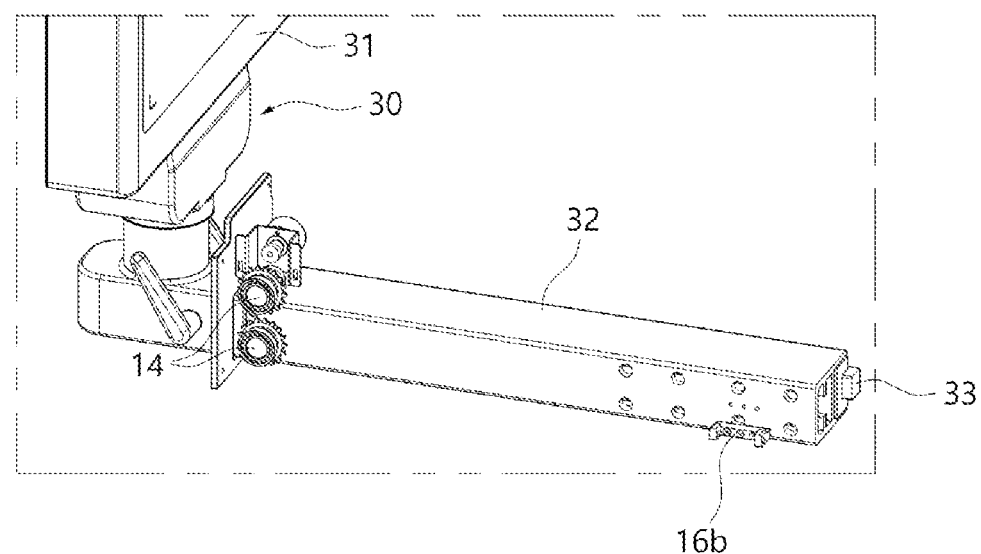
FIG. 5 is a view illustrating a detector arm of the detector according to the present disclosure.
Figure 6:
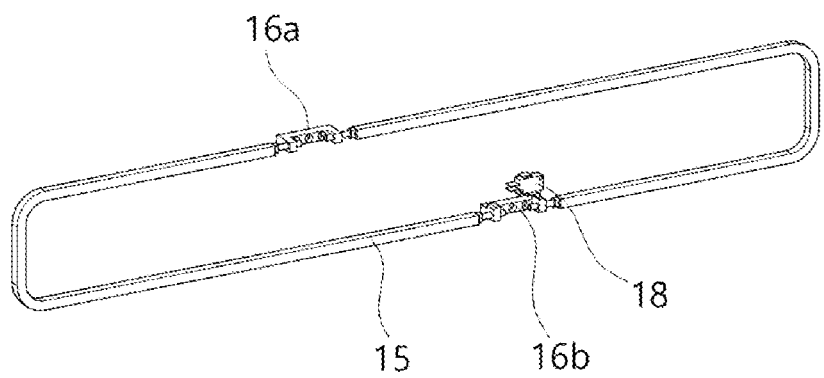
FIG. 6 is a view illustrating a gearless chain, and a chain connection block of the main arm according to the present disclosure.
Figure 7A:
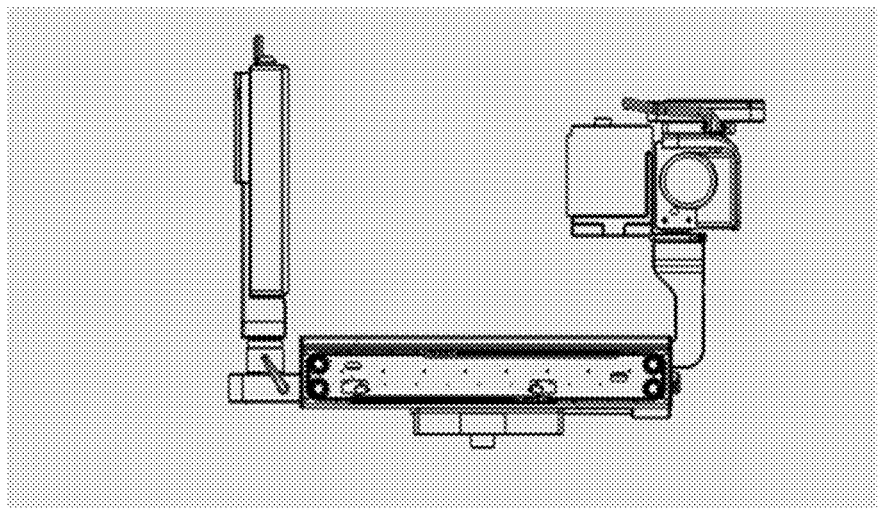
Figure 7B:
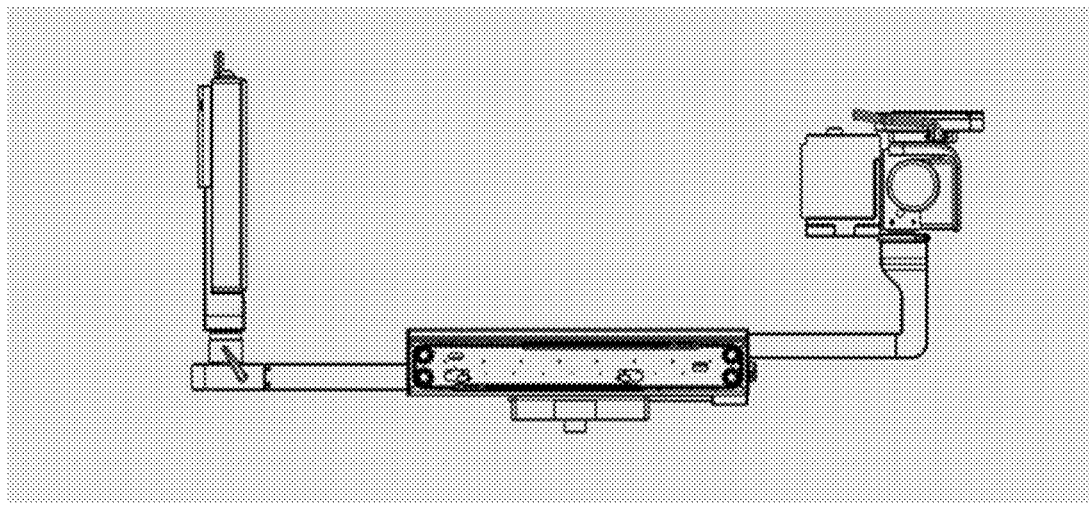

As illustrated in FIGS. 3, 7A, and 7B, a detector arm 32 of the detector 30 and a tube arm 22 of the imaging module 20 are accommodated in the main arm 10 in a manner that is capable of be moved into and out of the main arm 10.

A gearless chain 15, a plurality of idle sprockets 14, a chain connection block 16, and a drive motor 12 are provided within the casing 11 of the main arm 10.

The chain connection block 16 is configured to include a first chain connection block 16a fastened fixedly to the tube arm 22 and a second chain connection block 16b fastened fixedly to the detector arm 32. The first chain connection block 16a and the second chain connection block 16b each have the shape of the symbol ⊂. Respective bottom surfaces of the first chain connection block 16a and the second chain connection block 16b are fastened fixedly to the tube arm 22 and the detector arm 32, respectively. Opposite sidewalls of each of the first chain connection block 16a and the second chain connection block 16b are connected to the gearless chain 15.

The gearless chain 15 is configured to include a pair of chains arranged in such a manner as to face each other. A first end portion of one chain constituting the pair is configured in such a manner as to be connected to the first chain connection block 16a, and a second end portion thereof is configured in such a manner as to be connected to the second chain connection block 16b. A first end portion of the other one chain constituting the pair is configured in such a manner as to be connected to the second chain connection block 16b, and a second end portion thereof is configured in such a manner as to be connected to the first chain connection block 16a.

As described above, the chain connection block 16, the gearless chain 15, the detector arm 32, and the tube arm 22 are configured in such a manner to be moved or rotated in conjunction with each other.

The drive motor 12 is supported fixedly on the casing 11 of the main arm 10 through a bracket or the like inside of the main arm 10. A power transfer gear 13 is connected to the drive motor 12. The power transfer gear 13 is configured to rotate with rotary power of the drive motor 12. As illustrated in FIG. 3, any one of the idle sprockets 14 is connected coaxially to the power transfer gear 13. The idle sprocket 14 is configured in such a manner as to be rotated with rotation of the power transfer gear 13.

Four sprockets 14 are mounted on four edges, respectively, of the main arm 10 within the casing 11 of the main arm 10. Any one of the idle sprockets 14 is mounted coaxially on the power transfer gear 13. The idle sprocket 14 is connected to the gearless chain 15 and thus changes a direction of movement of the gearless chain 15.

When the power transfer gear 13 is rotated by driving the drive motor 12, one idle sprocket 14 connected to the power transfer gear 13 is rotated. At this point, the direction of movement of the gearless chain 15 connected to the idle sprocket 14 is changed by the idle sprocket 14. Thus, the gearless chain 15 is rotated clockwise or counterclockwise.

A proximity sensor 18 is provided within the casing 11 of the main arm 10. According to the present embodiment, the proximity sensor 18 is mounted at a predetermined position on a line along which the second chain connection block 16b moves. The proximity sensor 18 is configured in such a manner as to detect the chain connection block 16b and transmit a resulting detection signal when the chain connection block 16b is moved with rotation of the gearless chain 15 and thus is brought into contact with the proximity sensor 18 or is positioned at a position close to the proximity sensor 18. When the proximity sensor 18 detects that the second connection block 16b is moved to a predetermined position, a controller (not illustrated) may interrupt the driving of the drive motor 12 and thus may interrupt the movement of the gearless chain 15.

The imaging module 20 and the detector 30 are provided on both sides, respectively, of the main arm 10. Each of the detector arm 32 and the tube arm 22 is accommodated within the main arm 10. The detector arm 32 and the tube arm 22 are moved slidably in conjunction with each other in such a manner as to expand and contract in opposite directions with the main arm 10 in between.

The imaging module 20 includes an X-ray imaging tube 21 and the tube arm 22 supporting the X-ray imaging tube 21. One side of the tube arm 22 supports the X-ray imaging tube 21, and, for accommodation, the other side thereof is inserted into the main arm 10. The tube arm 22 has the shape of approximately a rectangular parallelepiped. A first LM guide 23 is mounted within the tube arm 22. The first chain connection block 16a is fastened fixedly to an external flanks surface of the tube arm 22.

The detector 30 includes an X-ray detection module 31 and the detector arm 32 supporting the X-ray detection module 31. One side of the detector arm 32 supports the X-ray detection module 31, and, for accommodation, the other side thereof is inserted into the main arm 10. The detector arm 22 has the shape of approximately a rectangular parallelepiped. A second LM guide 33 is mounted within the detector arm 22. The second chain connection block 16b is fastened fixedly to the outside of the detector arm 32.

According to the present embodiment, it is desirable that the detector 30 and the imaging module 20 are configured in such a manner as to have the same weight.

The detector 30 and the imaging module 20 are configured to have the same weight. Accordingly, the main arm 10 may maintain weight equilibrium because the weights on both sides thereof are the same and thus cancel each other out. Therefore, with small motive power, it is possible that the detector 30 and the imaging module 20 are driven slidably for expansion and contraction.

The X-ray imaging stand 1 according to the present disclosure that is configured as described causes the detector arm 32 and the tube arm 22 to expand and contract in opposite directions with the main arm 10 in between in such a manner that the detector arm 32 and the tube arm 22 are moved away from or toward each other in conjunction with each other.

The idle sprocket 14 and the gearless chain 15 are rotated clockwise by driving the drive motor 12. Thus, the tube arm 22 connected to the first chain connection block 16a connected to the gearless chain 15 and the detector arm 32 connected to the second chain connection block 16b connected to the gearless chain 15, as illustrated in FIG. 7B, are moved away slidably from each other.

In addition, the idle sprocket 14 and the gearless chain 15 are rotated counterclockwise by driving the drive motor 12 in the reverse direction. Thus, the tube arm 22 connected to the first chain connection block 16a connected to the gearless chain 15 and the detector arm 32 connected to the second chain connection block 16b connected to the gearless chain 15 are moved slidably toward each other.

Accordingly, the detector arm 32 and the tube arm 22 are controlled to expand and contract in conjunction with each other.

Although the specific embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An X-ray imaging stand with a straight arm structure, the X-ray imaging stand comprising:
    a detector comprising an X-ray detection module and a detector arm configured to support the X-ray detection module;
    an imaging module comprising an X-ray imaging tube and a tube arm configured to support the X-ray imaging tube;
    a main arm, each of the detector and the imaging module being connected to the main arm; and
    a stand main-body configured to force the main arm to ascend and descend and to be rotated,
    wherein the detector and the imaging module are configured in such a manner as to have the same weight, and the detector arm and the tube arm are both accommodated within the main arm, and are moved slidably in conjunction with each other in such a manner as to expand and contract in opposite directions with the main arm in between,
    wherein the main arm comprises:
    a first chain connection block fastened to the tube arm;
    a second chain connection block fastened to the detector arm; and
    a gearless chain, the first chain connection block and the second chain connection block being connected to the gearless chain.

2. The X-ray imaging stand of claim 1, wherein the gearless chain is configured to include a pair of chains arranged in such a manner as to face each other, opposite end portions of each chain being connected to the first chain connection block and the second channel connection block, respectively.

3. The X-ray imaging stand of claim 1, wherein the main arm comprises:
    a plurality of idle sprockets mounted on four edges, respectively, of the main arm and configured to change a direction of movement of the gearless chain;
    a power transfer gear connected coaxially to any one of the plurality of idle sprockets; and
    a drive motor configured to rotate the power transfer gear.

4. The X-ray imaging stand of claim 1, wherein a linear motion (LM) guide is mounted on each of the detector arm and the tube arm.

5. The X-ray imaging stand of claim 1, wherein the main arm further comprises:
    a proximity sensor being mounted at a predetermined position on the main arm and detecting that the first chain connection block or the second chain connection block approaches the proximity sensor.

6. The X-ray imaging stand of claim 3, wherein the detector arm and the tube arm are controlled to expand and contract in conjunction with each other:
    in such a manner that the sprocket and the gearless chain are rotated by driving the drive motor so that the tube arm connected to the first chain connection block connected to the gearless chain and the detector arm connected to the second chain connection block connected to the gearless chain are moved away slidably from each other; and
    in such a manner that the sprocket and the gearless chain are rotated counterclockwise by driving the drive motor in the reverse direction so that the tube arm connected to the first chain connection block connected to the gearless chain and the detector arm connected to the second chain connection block connected to the gearless chain are moved slidably toward each other.

* * * * *